United States Patent
Dekoninck et al.

(10) Patent No.: US 6,192,874 B1
(45) Date of Patent: Feb. 27, 2001

(54) DEVICE FOR MEASURING OXYGEN CONTENT IN A GAS MEDIUM

(75) Inventors: Christophe Dekoninck, Menucourt; Louis Delgrange, Le Port-Marly; Luc Herbin, Asnieres; Pierre Neyrat, La Norville; Frédéric Aimard, Rueil; Jean-Marie Taupin, Clamart, all of (FR)

(73) Assignee: Sagem SA, Paris (FR)

( * ) Notice: Subject to any disclaimer, the term of this patent is extended or adjusted under 35 U.S.C. 154(b) by 0 days.

(21) Appl. No.: 09/355,310

(22) PCT Filed: Jan. 28, 1998

(86) PCT No.: PCT/FR98/00155

§ 371 Date: Sep. 7, 1999

§ 102(e) Date: Sep. 7, 1999

(87) PCT Pub. No.: WO98/34102

PCT Pub. Date: Aug. 6, 1998

(30) Foreign Application Priority Data

Jan. 31, 1997 (FR) .................................. 97 01086

(51) Int. Cl.[7] .......................... G01N 27/406; F02D 41/14
(52) U.S. Cl. ........................ 123/697; 123/672; 123/693; 701/109
(58) Field of Search ..................... 123/672, 693, 123/694, 697–700, 703; 701/102, 103, 109; 73/23.32; 204/406, 408, 424–429; 205/784, 784.5, 785

(56) References Cited

U.S. PATENT DOCUMENTS

| 4,272,329 | * | 6/1981 | Hetrick et al. | 204/1 T |
| 4,543,176 | * | 9/1985 | Harda et al. | 204/406 |
| 4,601,809 | * | 7/1986 | Kitahara | 204/406 |
| 5,700,367 | * | 12/1997 | Yamada et al. | 205/785 |
| 5,781,878 | * | 7/1998 | Mizoguchi et al. | 701/109 |
| 5,869,744 | * | 2/1999 | Suzuki et al. | 73/23.32 |
| 6,009,866 | * | 1/2000 | Sagisaka et al. | 123/681 |

FOREIGN PATENT DOCUMENTS

| 3835958 A1 | * | 5/1989 | (DE) . |
| 0079085 A2 | * | 5/1983 | (EP) . |
| 015383 A1 | * | 9/1985 | (EP) . |
| 0444674 A2 | * | 9/1991 | (EP) . |
| 0507149 A1 | * | 10/1992 | (EP) . |
| 0740150 A1 | * | 10/1996 | (EP) . |
| 2177800A | * | 1/1987 | (GB) . |

* cited by examiner

Primary Examiner—Bentsu Ro
(74) Attorney, Agent, or Firm—Larson & Taylor, PLC

(57) ABSTRACT

The apparatus includes a sensor capable of delivering a voltage representative of the ratio between a reference oxygen pressure and the oxygen pressure in a volume of the sensor and provided with electrodes (12, 14) via which it is possible to pass a pumping current that controls said oxygen pressure in the volume, and monitoring and control means including a digital controller (26) receiving said representative voltage on an input and suitable for delivering the pumping current. The monitoring and control means deliver the pumping current in the form of a current that varies continuously and progressively, without interruptions, governed by the digital controller in such a manner as to servo-control the input voltage to a determined value.

11 Claims, 3 Drawing Sheets

DEVICE FOR MEASURING OXYGEN CONTENT IN A GAS MEDIUM

BACKGROUND OF THE INVENTION

The invention relates to apparatuses for measuring the oxygen content of a gaseous medium, the apparatuses being of the type comprising:

a sensor capable of delivering a voltage representative of the ratio between a reference oxygen pressure and the oxygen pressure in a volume of the sensor which communicates with the gaseous medium via a porous wall; and monitoring and control means enabling a pumping current to be delivered to cause oxygen to migrate away from or into said volume.

Numerous apparatuses of that type are already known, such as those described in EP-A-0 507 149 and U.S. Pat. No. 4,932,238. The sensor has at least one sensitive element constituted by a solid electrolyte plate of a type that allows oxygen ions to migrate, the plate being placed between two porous electrodes.

Such a sensor can be the subject of numerous embodiments. FIG. 1 is a diagram of a sensor that can be considered as having two cells. A first cell referred to as a "pumping" cell $10_p$ is sandwiched between two electrodes 12 and 14. The pumping cell $10_p$ is fixed to a second cell $10_s$, referred to as the "sensitive" cell, via a porous intermediate sheet so as to define a volume 18. Oxygen in the gaseous medium tends to penetrate into the volume 18 so as to bring the oxygen partial pressures into equilibrium. The passage of a current $I_p$ through the pumping cell tends to cause the oxygen contained in the volume to migrate, and thus to maintain the partial pressure therein at a determined value. A final plate 20 can be placed in contact with the sensitive element $10_s$ and can be made of the same material so as to deliver a constant reference pressure; its usefulness appears below.

Between the electrodes on either side of the sensitive element $10_s$ there thus appears a measurement voltage $V_s$ representative of the ratio between the partial pressures of oxygen in the volume 18 and in the plate 20 in contact with the cell $10_s$. Appropriate solid electrodes, and in particular of doped zirconium oxide or zirconia, have characteristics such that the voltage $V_s$ varies in substantially logarithmic manner with oxygen partial pressure in the volume 18. Conventionally, the current $I_p$ is controlled so as to maintain $V_s$ at a constant value, in which case $I_p$ is representative of the oxygen partial pressure in the gaseous medium. A heating resistor 21 serves to raise the cells to a suitable temperature.

In another embodiment, that can be described as a single cell embodiment and as shown in FIG. 2, the volume 18 is defined solely by the porous intermediate sheet 16 and by the cell $10_p$. The reference oxygen partial pressure is then that of atmospheric air, which is in contact with the cell $10_p$. Under such circumstances, variation of $I_p$ as a function of $V_p$ for different oxygen partial pressures has the general appearance shown in FIG. 3. Insofar as it is desired to remain at all times within a rectilinear portion of the characteristic, the value to which $V_p$ is servo-controlled must depend to some extent on the partial pressure of oxygen in the gas and on the impedance of the cell.

A major application of the invention lies in determining the air/fuel ratio admitted into an internal combustion engine on the basis of the composition of the exhaust gas, and more particularly on the basis of the partial pressure of the residual oxygen in the exhaust gas.

Until now, use has been made above all of sensors of the kind shown in FIG. 1. Often the monitoring and control means are constituted by an analog loop for servo-controlling $V_s$ to a constant value, associated with a microcontroller which deduces the oxygen partial pressure and the instantaneous richness of the mixture from the value of the current $I_p$. That solution suffers from drawbacks. The accuracy with which richness is measured is limited by the accuracy with which $I_p$ is measured. Embodiment in hard-wired form reduces possibilities of adjustment and matching.

SUMMARY OF THE INVENTION

It is an object of the invention to provide improved apparatus another object is to satisfy practical requirements better than previously known apparatuses, at low cost, and enabling richness to be measured accurately.

To this end, the invention provides in particular apparatus of the above-defined type in which the monitoring and control means have a digital controller receiving said voltage on its input and delivering the pumping current to the sensor in the form of a current that varies continuously and progressively without interruptions, and governed by the digital controller in such a manner as to servo-control said voltage on a determined value. The architecture can be such that the microcontroller has means for acting on the current $I_p$, thereby providing greater flexibility in adjusting the servo-control, good protection for the sensor, and finer management of putting into action and of degraded mode.

An advantageous solution consists in providing a digital controller that delivers a control voltage which is time modulated (e.g. by pulse width modulation) and in providing a lowpass filter and a current generator at the input of the sensor. Such modulation is easily performed by means of a digital controller. The presence of the filter avoids the need to apply interrupted pulses to the sensor which would reduce its lifetime.

The sensors have integrating behavior. It is advantageous to compensate it by subjecting said voltage representative of the ratio to processing that introduces a derivative component, prior to application to the digital controller. This increases the signal-to-noise ratio and enables the controller to reduce response time. In general, an amplifier circuit is provided to amplify the proportional component, and also the derivative component if present, prior to application to the digital controller.

The invention is applicable to apparatuses in which the sensor has a single cell separating the volume which communicates with the gaseous medium from a zone in which there exists a reference pressure; the representative voltage is then taken from the two electrodes on either side of the cell, and the pumping current is applied to the same cell. Nevertheless, the invention is more usually applied to apparatuses in which the sensor has two cells. Such a sensor has a volume defined by a porous intermediate sheet, by a first cell or "pumping" cell separating the volume from a zone occupied by the gas whose oxygen partial pressure is to be measured, and by a second cell or "sensitive" cell in contact with the reference pressure, with the representative voltage being taken from the electrodes on either side of the second cell. The pumping current then passes through the two electrodes on either side of the pumping cell.

In general, it can be considered that the main advantages of the apparatus stem from the fact that the digital controller has complete control over the pumping current $I_p$, both in normal servo-control mode and during transient stages (starting up, protecting the probe, diagnostics, . . . ), and that it serves to produce the current rather than to read back a current that is produced by external means as in present architectures.

Also, the apparatus:

firstly takes advantage of an analog portion that delivers an amplified signal on the basis of the sensor voltage $V_s$, which signal fortunately has a derivative component of accuracy that is not degraded by analog-to-digital conversion situated downstream from the preparation of said derivative component; and also makes it possible to produce the current $I_p$ by time modulation in the digital controller, which modulation, in association with a lowpass filter and a current controller governed by the filtered command delivers a pumping current $I_p$ that is variable continuously, progressively, and without interruptions, under the control of the digital controller.

Said current $I_p$ is then produced in a form that does not require an integrated digital-to-analog converter, even though such a converter can constitute a solution when the digital controller has one.

There exist stages in the operation of the apparatus during which the sensor would run the risk of being damaged if normal operating mode were to be maintained. For example, the normal operating conditions for apparatus having two cells consist in maintaining the voltage $V_s$ as measured on the second cell at a reference value and in deducing the oxygen content from the value of the pumping current $I_p$. That mode of operation requires the probe to be at a sufficiently high temperature, generally in the range 650° C. to 90° C. The sensor is raised to this temperature by a heating resistor. During an interval of time starting from the beginning of heating, the apparatus is inoperative because its temperature is too low. Nevertheless, it is desirable to obtain meaningful measurements as soon as possible, even if they are less accurate, together with an indication of the instant from which the measurements can be used.

In addition, various operating conditions make the normal mode of operation liable to degrade the sensor because they lead to too high a voltage $V_p$ across the pumping cell.

In an advantageous embodiment of the invention, and under conditions that make the normal mode inappropriate, the apparatus can obtain measurements that are degraded, but nevertheless of use.

For this purpose, the monitoring and control means can include means for switching between servo-controlling the voltage of the sensitive cell on a constant value and limiting the voltage of the pumping cell to a ceiling value, suitable for protecting the sensor.

In particular, the controller can be designed to initialize operation by controlling the pumping current $I_p$ so as to limit the voltage $V_p$ across the pumping cell to a maximum value that is compatible with protecting the cell, and then in repeating the following sequence:

the pumping current is servo-controlled to the voltage applied to the sensitive cell, while verifying that the voltage across the pumping cell remains below the ceiling; and the pumping current is again governed so that it is compatible with the ceiling insofar as the ceiling is exceeded during the servo-control of the voltage $V_s$ applied to the sensitive cell.

More generally, the digital controller can be designed to use the voltages measured across the terminals of both cells and to take the pumping current $I_p$ into account in order to perform additional functions, such as:

estimating the temperature of the probe, in order to determine the instant at which it becomes usable;

diagnosing aging; and operating in degraded mode, with servo-control being applied to the voltage $V_p$ of the pumping cell instead of to the voltage $V_s$.

When operating in degraded mode, $V_p$ need not be servo-controlled to a fixed value, but to a value that is selected so as to take account of other parameters or of the function to be performed, such as calibration, diagnosis, or operating in degraded mode due to abnormal conditions.

The above characteristics and others will appear better on reading the following description of particular embodiments given as non-limiting examples. The description refers to the accompanying drawings.

DETAILED DESCRIPTION OF PREFERRED EMBODIMENTS

Figure 1:
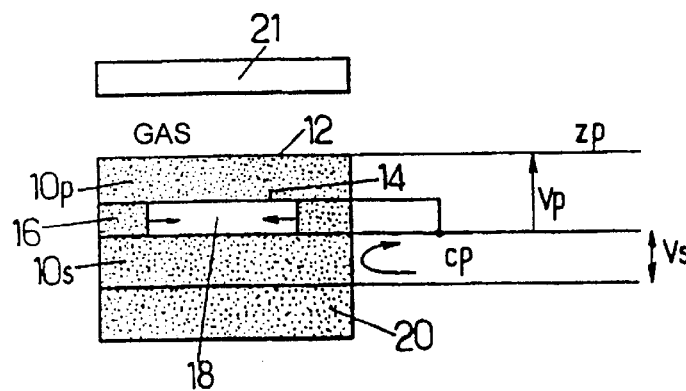
FIGS. 1 and 2, already mentioned above, show respectively a two-cell sensor and a one-cell sensor.
Figure 2:
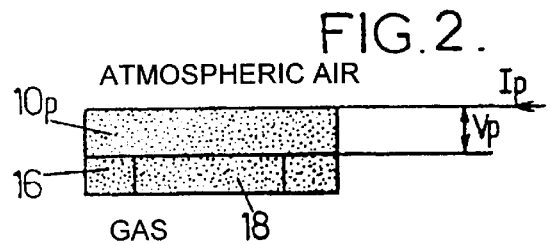
Figure 3:
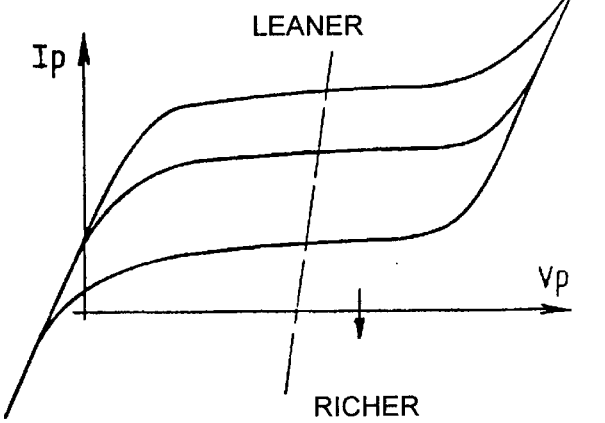
FIG. 3 is a graph in which the curves show pumping current variation as a function of voltage across the pumping cell for various partial pressures of oxygen in the surrounding atmosphere.
Figure 4:
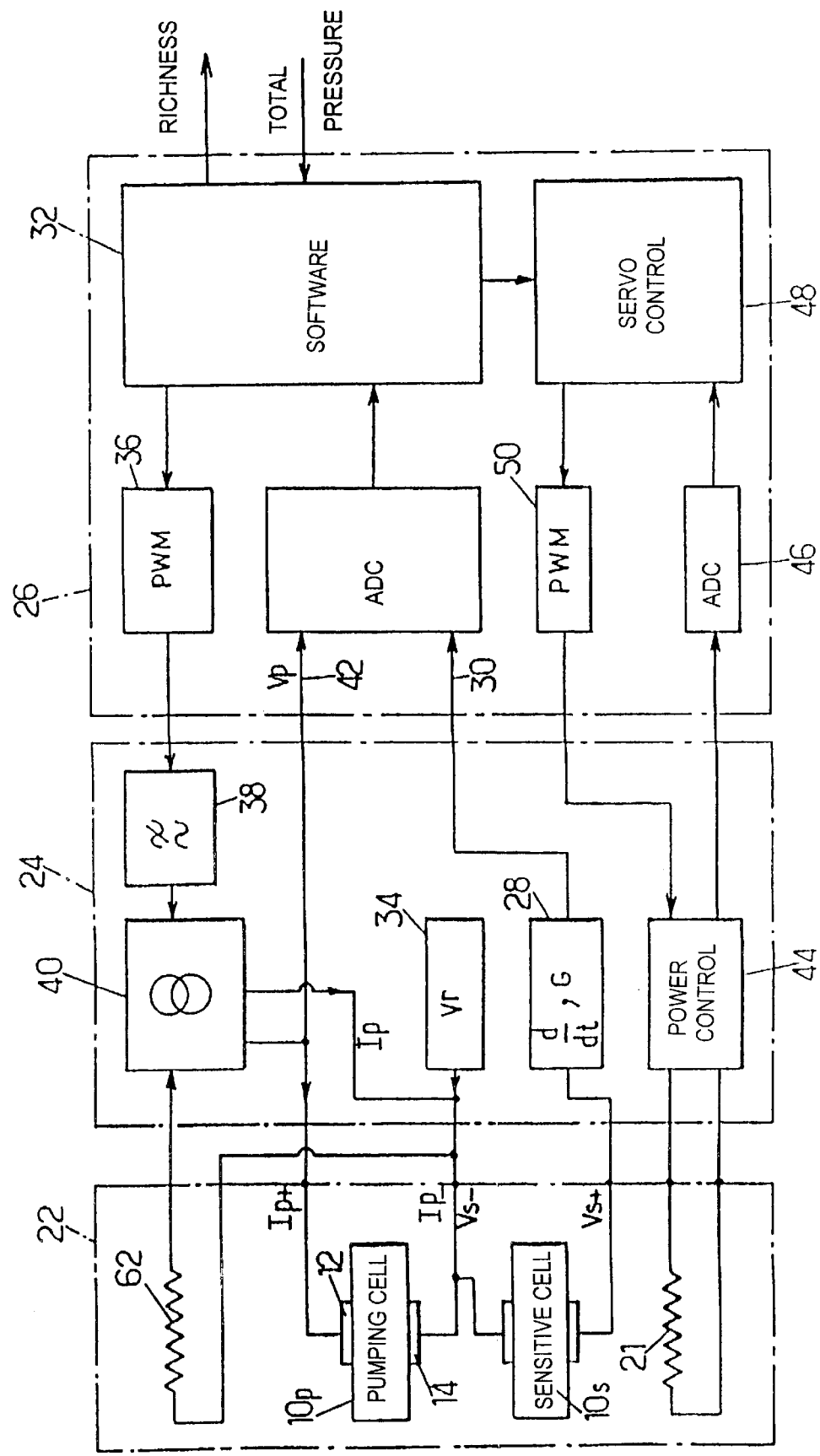
FIG. 4 is a block diagram of apparatus of the invention.

The apparatus whose general structure is shown in FIG. 4 comprises a sensor 22 whose structure is as shown in FIG. 1. That is why elements corresponding to elements in FIG. 1 are given the same reference numerals.

The monitoring and control means associated with the sensor 22 can be thought of as having a "hardware" or hard-wired portion 24 and a digital controller 26 constituting a "software" portion.

In normal and stabilized operation of the apparatus, the monitoring and control means receive the voltage across the terminals of the sensitive cells $10_s$ which appears between terminals $V_s-$ and $V_s+$, and they deliver a pumping current to the sensor, which current flows between the terminals $I_p+$ and $I_p-$. Ground connections and power supplies are not shown in FIG. 4 in order to simplify the figure.

The voltage $V_s$ is processed in the hardware portion 24 by an analog circuit 28 for introducing a derivative component and for amplification with gain G. The signal as processed in this way is applied to the digital controller 26. It is digitized therein by a digital-to-analog converter (DAC) which receives the signal on an input 30. In an application of the apparatus to controlling an internal combustion engine, a converter operating on eight to ten bits is generally sufficient. The controller includes software, represented at 32, for governing the servo-control $V_s$ on a constant value, which value can be fixed by a generator 34 that generates a reference voltage $V_r$. The servo-control is advantageously selected so that the set point value of $V_s$ is substantially in the middle of a linear portion of the $I_p(V_s)$ characteristic.

The software 32 is designed to deliver a signal that is fed to the circuit 36 that delivers a time-modulated voltage signal, generally using pulse width modulation (PWM). Such digital components and programs serving to transform a digital input signal into a signal modulated in this way are commonly available.

The pulse width modulated signal, of variable duty ratio, is applied to a lowpass filter 38 so as to transform it into a signal that is not interrupted, which signal is applied to a direct current generator 40 that delivers the current $I_p$. Given that the sensors generally present dispersion in the sensitivity of the characteristic of pumping current $I_p$ as a function of richness, the current generator 40 can be designed to take account of a compensation resistor 62 integrated in the sensor to normalize the characteristic of $I_p$ as a function of richness. Still in the special case of apparatus designed to be incorporated in an engine control system, pulse width modulation encoded on twelve bits provides sufficient resolution. The least significant bit can correspond, for example, to a change in the current $I_p$ of the order of 3 $\mu A$.

As mentioned above, certain stages of operation make it desirable to servo-control the voltage $V_p$ rather than the voltage $V_s$. To make this mode of operation possible, the digital controller 26 may include an analog-to-digital converter (ADC) whose analog input 42 receives the voltage VP taken from the terminal $I_p$+.

Satisfactory operation of the sensor requires the cells to be at an appropriate temperature, generally lying in the range 650° C. to 900° C. This temperature can be maintained by controlling the heat dissipated in a heater resistor 21. This control can include servo-control making use of the digital controller 26. In the case shown diagrammatically in FIG. 4, the resistor 21 is powered by an analog power control and current measuring circuit 44 connected to an analog input of an analog-to-digital converter 46 of the controller which may optionally be the same ADC as that provided with the inputs 30 and 42. The software 48 of the controller performs the servo-control function and the function of controlling an output modulator 50 which delivers a pulse width modulated signal controlling the circuit 44.

The way in which temperature servo-control operates for the purpose of maintaining the cells at a determined temperature can be as follows.

Initially, laws concerning variation in the resistance of the pumping cell as a function of temperature, for various oxygen concentrations (corresponding to various different degrees of mixture richness when feeding an engine) are loaded into the software portion 32 of the digital controller 26. In normal operation, it is known that a lean mixture is desirable, which leads to the presence of residual oxygen in the exhaust gas.

The software 32 then includes a program that periodically causes a current increment $\Delta I_p$ to be applied to the current $I_p$. This increment gives rise to a variation $\Delta V_p$ in the voltage $V_p$ as measured on the output $I_p$+. The controller 26 can determine this variation $\Delta V_p$ by taking the difference between two successive digital values that appear on the output of the input ADC 42. The resistance R of the pumping cell is given by the ratio $\Delta V_p/\Delta I_p$. Temperature is deduced therefrom by referring to a lookup table, stored in digital form in the software 32. The corresponding information can be transmitted to the governing software 48 for modifying the current flowing through the heater resistor 21 accordingly.

For a sensor that has only one cell, a voltage $E_p$ to be regulated on a value of about 450 mV, for example, on the basis of known values for $V_p$ and $I_p$. Use is then made of an estimate of the resistance R of the single cell as given by:

$$R=\Delta V_p/\Delta I_p$$

The apparatus of FIG. 4 also makes it possible to protect the sensor while continuing with degraded operation, by limiting the voltage $V_p$. For this purpose, the digital controller compares $V_p$ with a stored maximum value, which value can be fixed or which can vary as a function of external parameters. If $V_p$ tends to exceed the threshold value, the servo-control mode is modified. The current $I_p$ is controlled to maintain the voltage $V_p$ at the maximum authorized value. This generally implies returning at regular intervals to an attempt at servo-controlling the pumping current to the voltage $V_s$, and then immediately returning to servo-controlling $V_p$ in the event of $V_p$ exceeding the acceptable value.

Figure 6:
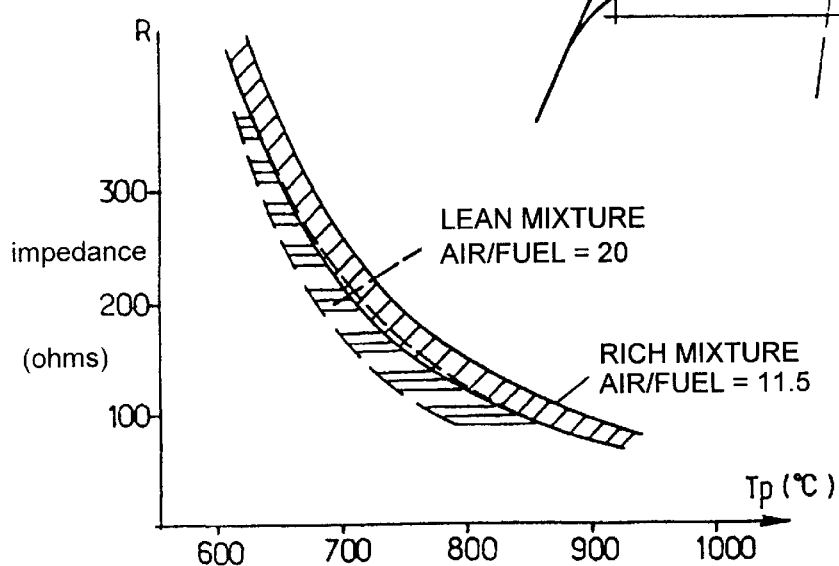
FIG. 6 shows how the resistance of the pumping cell varies as a function of temperature for a rich mixture and for a mixture that is relatively lean.

Operation of the apparatus can be initialized (sensor cold) as follows, at least when the apparatus is integrated in an engine control system. Under such circumstances, starting is performed using a mixture that is rich, i.e. with a law for variation of impedance as a function of temperature as given by dashed lines in FIG. 6. The digital controller 26 is designed to attempt initially to operate the probe with servo-control of the voltage $V_p$ and with evaluation of the resistance R at a high rate. Under such circumstances, meaningful measurements, although less accurate than those taken in normal operation, can be obtained and validated as soon as the measured resistance R shows that the temperature has reached a first value, e.g. in the range 550° C. to 650° C. A changeover to attempting to servo-control $V_s$ can be programmed on reaching a determined value for the resistance R.

Figure 5:
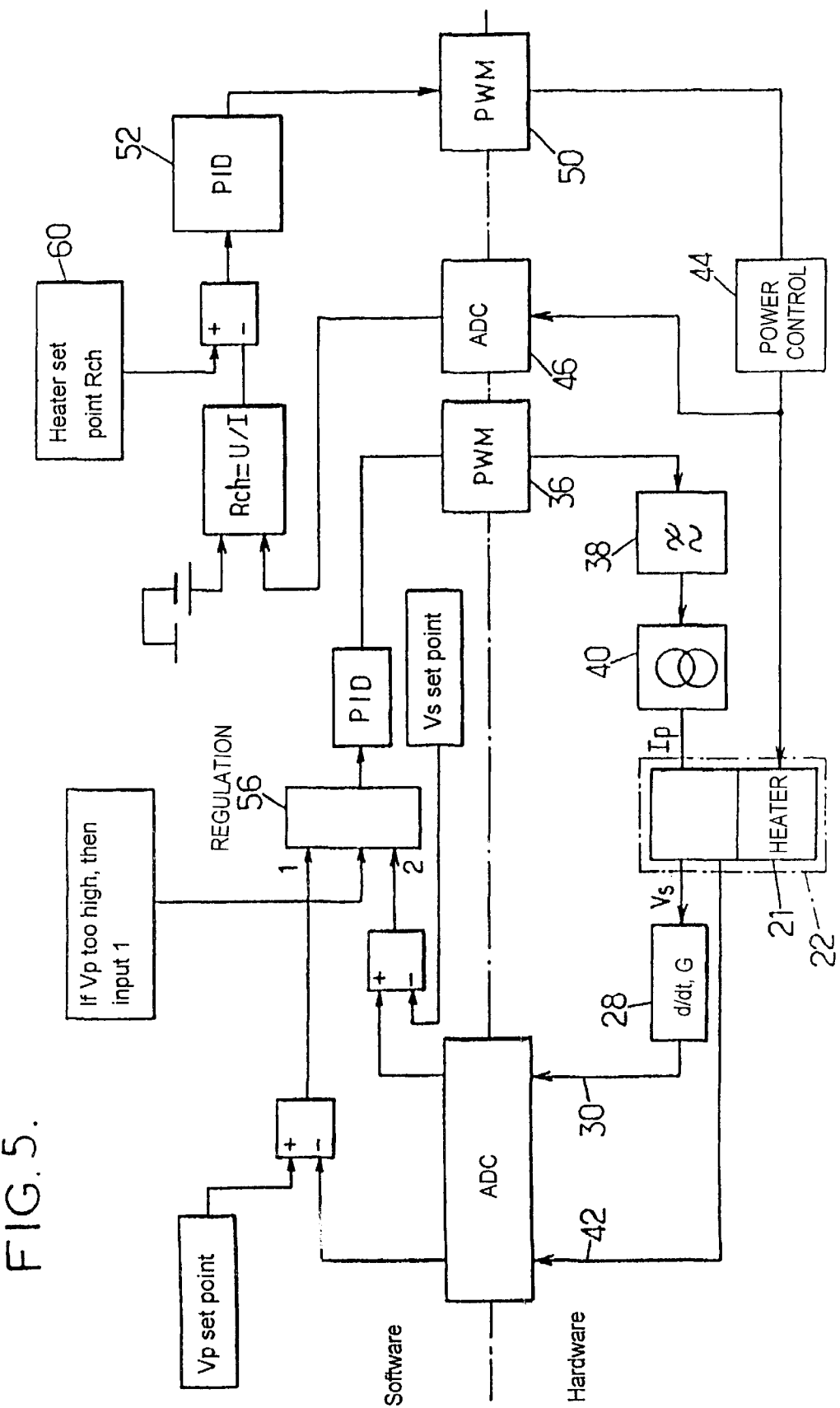
FIG. 5 is a diagram for showing the way functions are shared between hardware and software in a particular embodiment.

The way in which functions are shared between the hardware portion and the software portion can be as shown in FIG. 5, where functions are designated by the same reference numerals as the corresponding components in FIG. 4. The interface between the software portion and the hardware portion comprises the inputs 30 and 42 and the input to the analog-to-digital converter 46; the converters can have 10-bit outputs. The interface also comprises the pulse width modulator circuits 36 and 50. The modulator circuit 36 can operate at a frequency of 5 kHz and can have a 12-bit output. The modulator circuit 50 will generally operate at a much lower frequency, e.g. about 30 Hz.

The heating resistor can be regulated in conventional manner so as to maintain its resistance at a determined value fixed by a set point 60. A proportional-integral-derivative type stabilization circuit 52 can be provided.

As mentioned above, the controller includes a program for testing the temperature of the sensor and for testing the value of $V_p$, acting at 56 to direct regulation either to maintaining $V_s$ at a set point value for $V_s$ (input 2), or maintaining $V_p$ at a set point value (input 1).

What is claimed is:

1. Apparatus for measuring the oxygen content of a medium, the apparatus comprising:

a sensor having a porous wall for communicating a volume thereof with said medium arranged for delivering a voltage representative of the ratio between a reference oxygen pressure and oxygen pressure in a fraction of said medium present in a volume of the sensor, and provided with electrodes enabling a pumping current to be passed for controlling said oxygen pressure in the volume; and monitoring and control means including a digital controller connected to receive said representative voltage on an input thereof and arranged for delivering the pumping current;

the apparatus being characterized in that the monitoring and control means deliver pumping current in the form of a current that varies continuously and progressively, without interruptions, governed by the digital controller to servo-control said representative voltage and to maintain said representative voltage at a determined value.

2. Apparatus according to claim 1, characterized in that the monitoring and control means include a circuit that introduces a derivative component prior to said representative voltage being applied to the digital controller.

3. Apparatus according to claim 1, characterized in that the monitoring and control means include a circuit introducing gain to a proportional component of said representative voltage, and gain to a derivative component if present, prior to application to the digital controller.

4. Apparatus according to claim 1, characterized in that the sensor comprises a single cell separating the volume of a zone in which the reference pressure exists, in that the representative voltage is taken from two electrodes on either side of the cell, and in that the pumping current is applied to the same cell.

5. Apparatus according to claim 1, characterized in that the sensor has a volume defined by a porous intermediate sheet and by a first or "pumping" cell separating the volume from a zone occupied by the gas where the oxygen partial pressure is to be measured, and a second or "sensitive" cell in contact with the reference pressure, in which the representative voltage is taken from electrodes on either side of the second cell, and in that the pumping current passes through two electrodes on either side of the first cell.

6. Apparatus according to claim 5, characterized in that the monitoring and control means comprise means for changing-over from servo-controlling the voltage of the sensitive second cell to a constant value to limiting the voltage of the pumping cell to a predetermined ceiling value for protecting the sensor.

7. Apparatus according to claim 5, characterized in that the controller is designed to initialize operation by controlling the pumping current to limit the voltage ($V_p$) across the pumping cell to a maximum value compatible with protecting the sensor, and in repeating a pumping current servo-control sequence on the voltage ($V_s$) across the second cell while verifying that the voltage ($V_p$) remains below a ceiling, and returning to governing the pumping current so that it is compatible with the ceiling of $V_p$ insofar as the ceiling is exceeded by servo-control governing of $V_s$.

8. Apparatus according to claim 5, characterized in that said monitoring and control means include means for evaluating the resistance of the pumping cell, having means for periodically applying a temporary increment to the pumping current and for measuring the corresponding change in the voltage of said cell.

9. Apparatus according to any preceding claim, characterized in that the controller also performs engine control functions.

10. Apparatus for measuring an oxygen content in exhaust gas of an internal combustion engine, comprising:
  a sensor for delivering a voltage representative of a ratio between a reference oxygen pressure and oxygen pressure in a volume of the sensor, communicating with said exhaust gas by a porous wall provided with electrodes enabling a pumping current to be passed for pumping oxygen out of the volume and controlling said oxygen pressure in the volume; and
  monitoring and control means including:
    digital controller means connected to receive said representative voltage on an input thereof and arranged to deliver a time-modulated control voltage,
    and a series arrangement of a lowpass filter and a current generator connected to receive said time modulated control voltage and arranged for delivering said pumping current to said electrodes of the sensor in the form of a current having steady variations without time interruptions,
    said digital controller means being programmed to continuously adjust said time modulated control voltage for maintaining the representative voltage at a predetermined value, whereby said pumping current is a representation of said oxygen content.

11. Apparatus according to claim 10, characterized in that the digital controller delivers at its output a signal for governing the monitoring and control means, which signal is constituted by a pulse width modulated voltage.

* * * * *